United States Patent [19]

Heeres et al.

[11] Patent Number: 4,602,010

[45] Date of Patent: Jul. 22, 1986

[54] FUNGICIDAL 1-(-2-ARYL-4,5-DISUBSTITUTED-1,3-DIOXO-LAN-2-YLMETHYL)-1H-IMIDAZOLES AND 1H-1,2,4-TRIAZOLES

[75] Inventors: Jan Heeres, Vosselaar; Leo Backx, Arendonk; Willy Van Laerhoven, Beerse, all of Belgium; Elmar Sturm, Aesch, Switzerland

[73] Assignee: Janssen Pharmaceutica, N.V., Beerse, Belgium

[21] Appl. No.: 549,041

[22] Filed: Nov. 7, 1983

Related U.S. Application Data

[60] Continuation of Ser. No. 344,850, Feb. 1, 1982, abandoned, which is a division of Ser. No. 202,964, Nov. 3, 1980, Pat. No. 4,329,342, which is a continuation of Ser. No. 53,639, Jun. 29, 1979, abandoned.

[30] Foreign Application Priority Data

Jul. 24, 1978 [CH] Switzerland .......................... 7963/78
Jul. 25, 1978 [CH] Switzerland .......................... 8001/78

[51] Int. Cl.$^4$ .................. A01N 43/653; A01N 55/02; C07D 407/06; C07F 1/08
[52] U.S. Cl. ..................................... 514/184; 514/383; 548/101; 548/262
[58] Field of Search ................ 548/101, 262; 424/245, 424/269

[56] References Cited

U.S. PATENT DOCUMENTS

| | | | |
|---|---|---|---|
| 3,575,999 | 4/1971 | Godefroi et al. | 424/273 R |
| 4,156,008 | 5/1979 | Heeres | 424/273 R |
| 4,160,838 | 7/1979 | Van Reet et al. | 548/262 |

FOREIGN PATENT DOCUMENTS 2026486  2/1980  United Kingdom ................ 548/262

Primary Examiner—Alton D. Rollins
Attorney, Agent, or Firm—Geoffrey G. Dellenbaugh

[57] ABSTRACT

Novel 1-(1,3-dioxolan-2-ylmethyl)-1H-imidazoles and 1H-1,2,4-triazoles wherein the 1,3-dioxolane ring is substituted in the 4- and in the 5-positions, said compounds having useful antimicrobial properties.

6 Claims, No Drawings

FUNGICIDAL 1-(-2-ARYL-4,5-DISUBSTITUTED-1,3-DIOXOLAN-2-YLMETHYL)-1H-IMIDAZOLES AND 1H-1,2,4-TRIAZOLES

This application is a continuation of our copending application Ser. No. 344,850, filed Feb. 1, 1982, abandoned which in turn is a divisional application of Ser. No. 202,964, filed Nov. 3, 1980, now U.S. Pat. No. 4,329,342, which in turn is a continuation of application Ser. No. 53,639, filed June 29, 1979, now abandoned.

BACKGROUND OF THE INVENTION

In U.S. patent application Ser. No. 732,829, filed Oct. 15, 1976 and in U.S. Pat. Nos. 3,575,999 and 4,079,062 there are described a number of 1-(2-aryl-1,3-dioxan-2-ylmethyl)-1H-imidazoles and 1H-1,2,4-triazoles and a number of 1-(2-aryl-1,3-dioxolan-2-ylmethyl)-1H-imidazoles and 1H-1,2,4-triazoles, wherein the 1,3-dioxolane-moiety is substituted with one alkyl group or two methyl groups. The compounds of the present invention differ from the foregoing essentially by the presence of the 4 and 5 positions of the dioxolane ring of either two alkyl groups, one of which has at least 2 carbon atoms, or, a tetramethylene bridge.

DESCRIPTION OF THE PREFERRED EMBODIMENTS

This invention relates to novel 1-(2-aryl-1,3-dioxolan-2-ylmethyl)-1H-imidazole and 1H-1,2,4-triazole-derivatives having the formula

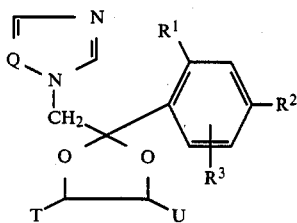

(I)

and the phytopharmaceutically acceptable acid addition salts, metal salt complexes and stereochemically isomeric forms thereof, wherein $R^1$, $R^2$ and $R^3$ are each independently selected from the group consisting of hydrogen and halo, provided that at least one of $R^1$, $R^2$ and $R^3$ is halo;

Q is a member selected from the group consisting of CH and N;

T is a member selected from the group consisting of methyl and ethyl;

U is a member selected from the group consisting of ethyl and propyl, or T and U, when taken together, may represent a tetramethylene radical which is optionally substituted with up to two methyl groups.

Preferred compounds within the scope of this invention are those wherein $R^1$ and $R^3$ are hydrogen, chloro or bromo and $R^2$ is chloro or bromo.

Particularly preferred compounds of formula (I) are those wherein $R^2$ is chloro and $R^1$ and $R^3$ are hydrogen and those wherein $R^1$ and $R^2$ are both chloro and $R^3$ is hydrogen.

Even more preferred compounds within the scope of the invention are those wherein Q is N and evenso the compounds wherein T and U represent a tetramethylene radical, preferably an unsubstituted tetramethylene radical.

The most preferred compounds within the scope of this invention are those wherein Q is N, T and U are unsubstituted tetramethylene, $R^1$ and $R^3$ are hydrogen and $R^2$ is chloro and evenso those wherein Q is N, T and U are unsubstituted tetramethylene, $R^1$ and $R^2$ are chloro and $R^3$ is hydrogen.

As used in the foregoing definitions the term halo is generic to fluoro, chloro, bromo and iodo; and propyl has the meaning of n. propyl and i. propyl.

This invention is also concerned with a method of preparing the compounds of formula (I), with anti-microbial compositions which comprise as an active ingredient an effective anti-microbial amount of a compound of formula (I) and also with a method of curing plant diseases by the use of compounds of formula (I).

The compounds of formula (I) can generally be prepared by the reaction of an azole of formula (II), wherein Q is as previously described and Me is hydrogen, a tetrasubstituted ammonium ion, e.g., tetra($C_1$–$C_6$-alkyl)ammonium, tri($C_1$–$C_6$-alkyl)ammonium and the like, or, preferably, a metal atom, most preferably, an alkali metal atom, e.g., sodium, potassium and the like, with a halogenide of formula (III) wherein $R^1$, $R^2$, $R^3$, T and U are as previously described and Y is halo, preferably chloro, bromo or iodo.

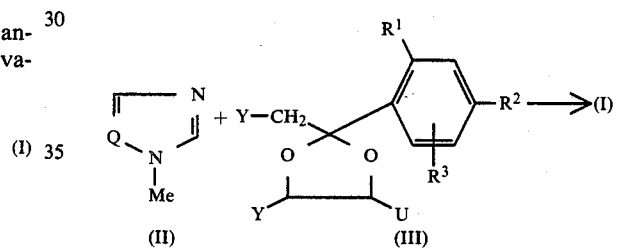

The reaction of (II) with (III) is preferably carried out in a relatively polar, reaction-inert organic solvent, such as, for example, N,N-dimethylformamide, N,N-dimethylacetamide, dimethylsulfoxide, acetonitrile, benzonitrile and the like. Such solvent can be used in combination with other reaction-inert solvents, e.g. aliphatic or aromatic hydrocarbons such as, for example, benzene, methylbenzene, dimethylbenzene, hexane, petroleumether, chlorobenzene, nitrobenzene and the like. When said Y represents chloro or bromo it may be advantageous to conduct the reaction in the presence of an alkali metal iodide, such as sodium or potassium iodide, to enhance the reaction rate. Elevated temperatures of from about 30° to about 220° C., preferably from about 80° to about 170° C. are appropriate and conveniently the reaction is carried out under reflux.

When Me represents hydrogen the reaction is carried out in the presence of a base. Suitable bases which may be utilized include alkali metal oxides, hydroxides, carbonates and hydrogen carbonates as well as tertiary amines such as N,N-diethylethanamine, pyridine and the like. In view of its basic properties the azole (II), when added in excess may be used to promote the reaction.

In these and the following preparations the reaction products may be isolated from the medium and, if necessary, further purified according to methodologics generally known in the art, such as, for example, extraction, trituration, crystallization, chromatography and the like.

Suitable salt forming acids are respectively well-tolerated by plants or physiologically acceptable, such as, for example, inorganic acids, e.g. hydrochloric-, hydrobromic-, hydroiodic-, sulfuric-, phosphoric-, phosphonic-, nitric- and the like acids, organic acids, e.g., trifluoroacetic-, trichloroacetic-, benzenesulfonic-, methanesulfonic-, and the like acids.

Metal salt complexes of formula (I) may be obtained by the complexation-reaction of an azole of formula (I) with an organic or inorganic metal salt such as, for example, hydrohalides, nitrates, sulfates, phosphates, 2,3-dihydroxybutanedioates and the like of copper, manganese, zinc, iron and the like transition metals, which may be present in each of their possible valencies.

Stoechiometrically defined metal salt complexes may be prepared by dissolving a compound of formula (I) in a water-miscible solvent (e.g. warm ethanol, methanol, 1,4-dioxane or N,N-dimethylformamide) and adding thereto an aqueous solution of the desired metal salts such as, for example, $CuSO_4.5H_2O$, $Mn(NO_3)_2.4H_2O$, $FeCl_3.6H_2O$ and the like.

The foregoing enumerations are intended to illustrate and not to limit the scope of the present invention.

The intermediates of formula (II), used as starting materials in the foregoing reactions, are generally known in the art.

The intermediates of formula (III) may be prepared according to art-known methodologies of preparing such or similar compounds, such as, for example, by acetalizing an appropriate acetophenone derivative of formula (IV) with an appropriate 1,2-diol of formula (V) following art-known acetalizing procedures.

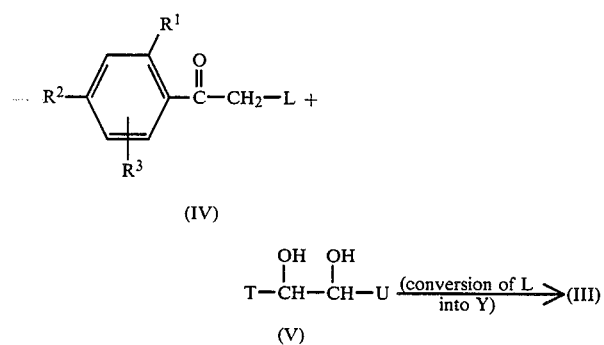

In the foregoing reaction-scheme $R^1$, $R^2$, $R^3$, T and U are as previously defined and L represents hydrogen or a radical Y. When L represents hydrogen, this L-group is converted into a halo-group following art-known halogenating procedures, before, during or after the acetalization. The acetalization-reaction is easily carried out by stirring and heating the reactants together in a suitable reaction-inert solvent, e.g., benzene, methylbenzene and the like, preferably in the presence of a catalytic amount of an appropriate acid, e.g., 4-methyl-benzenesulfonic acid and the like. Most preferably, the reaction is carried out under azeotropic destillation of the water which is liberated during the course of the reaction. Alternatively the acetals of formula (III) may be derived from other cyclic- or aliphatic acetals by reacting the latter with an excess of the 1,2-diol (V), corresponding to the desired acetal. In case T and U represent a tetramethylene radical which is optionally substituted with up to two methyl substituents the corresponding cis- and trans 1,2-cyclohexanedioles as well as mixtures containing both isomers may be used as 1,2-diol (V) yielding the cis and/or trans forms of the acetals of formula (III).

From formula (I) it is evident that the compounds of this invention have at least three asymmetric carbon atoms in their structures, namely those located in the 2-, the 4- and the 5-position of the dioxolane nucleus, and consequently they can exist under different stereochemically isomeric forms. The stereochemically isomeric forms of (I) and the phytopharmaceutically acceptable acid addition salts and metal salt complexes thereof are intended to be within the scope of this invention.

The diastereomeric racemates of (I) may be obtained separately by conventional methods. Appropriate methods which may advantageously be employed therefore include, for example, selective crystallization and chromatographic preparation, e.g., column chromatography.

Since the stereochemical configuration is already fixed in the intermediates (III) it is also possible to separate the diastereomeric racemates at this stage, whereupon the corresponding forms of (I) may be derived therefrom in the previously indicated manner. The separation of the diastereomeric racemates of such intermediates may be performed by conventional methods as described hereabove for the separation of the diastereomeric racemates of the compounds (I).

Particularly, the compounds of formula (I) possess a very advantageous antimicrobial spectrum, rendering them useful for the protection of crops without causing undesired side-reactions. Examples of crops within the scope of this invention are the followings: cereals, maize, rice, vegetables, sugar-beet, soybeans, groundnuts, fruit-trees, ornamentals, grapevines, hops, cucurbitaceae (gherkins, cucumbers, melons), solanaceae such as potatoes, tobacco and tomatoes, as well as bananas, cocoa and rubber.

The compounds of formula (I) can be used to reduce or destroy fungal growth on plants of these or related crops or on parts of such plants (e.g., fruits, blossoms, foliage, stams, tubers, roots), whereby the newly outgrowing parts of such plants are also protected against fungal attack. The compounds of this invention are active against phytopathogenic fungi belonging to the following classes: Ascomycetes (e.g. Erysiphaceae, Fusarium, Venturia, Helminthosporium); Basidiomycetes such as particularly rust-fungi (e.g. Puccinia); *Fungi imperfecti* (e.g. Moniliales etc., Cercospora and Botrytis) and Oomycetes belonging to the class of the Phycomycetes such as, for example, Phytophthora and Plasmopara. They can further be used as seeddressings for the treatment of seed (e.g. fruits, tubers, grains) and cuttings to protect them from fungal infection, and against fungi occuring in the soil.

Botrytis species (*Botrytis cincrea*, *Botrytis allii*) cause extensive economical damages with greymold to vines, strawberries, apples, bulbs and the like fruit and vegetables.

The compounds of formula (I) can be used alone or in admixture with appropriate carriers and/or additives. Appropriate carriers and additives can be solid or fluid and are generally known in the art of formulating, such as, for example, natural and regenerated mineral substances, solvents, dispersants, wetting agents, adhesives, thickners, binders or fertilizers.

The concentration of the active ingredient in commercial preparations can vary from about 0.1 to about 90%.

For their application the compounds of formula (I) can be formulated in the following composition-forms (whereby suitable concentrations of the active ingredient are indicated within brackets):

solid compositions: dusts
(up to 10%), granulates, coated granulates, impregnated granulates and homogeneous granulates, pellets (from 1 to 80%);

liquid compositions:
(a) water-dispersible concentrates: wettable powders and pastes (25–90% in commercial form, 0.01–15% in the ready for use solution); emulsion- and solution concentrates (10–50%; 0.01–15% in ready for use solution); (b) solutions (0.1–20%); aerosols.

If desired, in order to extend their spectrum of activity the compounds of formula (I) may be combined with other appropriate pesticides such as, for example, fungicides, bactericides, insecticides, acaricides, herbicides, plant-growth regulators and the like.

The following examples are intended to illustrate and not to limit the scope of the present invention. All temperatures are given in degrees Celsius.

A. EXAMPLES OF CHEMICAL PREPARATION

Example I

To a mixture of 86 g (1.3 mole) of pulverized potassium hydroxide (85%), 100 g (1.45 mole) of 1,2,4-triazole in 1000 ml of dimethylsulfoxide there is added during a period of 8 hours, while stirring and heating at 145°, under nitrogen atmosphere, a solution of 363 g (1.025 mole) of cis/trans 2-bromomethyl-2-(2,4-dichlorophenyl)-5-ethyl-4-methyl-1,3-dioxolane in 250 ml of dimethylsulfoxide. After completion the dark-brown mixture is stirred and heated for another 6 hours. After cooling, the mixture is taken up in 3 l of 1,1'-oxybisethane and 6 l of water, the layers are shaken and separated. The organic layer is washed till neutral, dried, filtered and evaporated, yielding a highly viscous brown oil, which, after destillation under reduced pressure yields 271 g (77.3%) of a high viscous yellow oil, b.p. 136°–152°/0.003 Torr, which crystallizes while standing. After 3 subsequent recrystallizations from a mixture of 2,2'-oxybispropane and hexane, there are obtained white crystals of [2-(2,4-dichlorophenyl)-4-ethyl-5-methyl-1,3-dioxolan-2-ylmethyl]-1H-1,2,4-triazole; mp. 109°–113°.

In a similar manner there are also prepared:

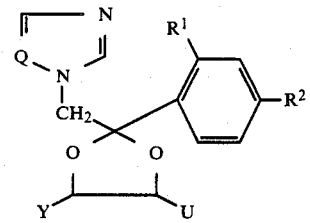

| Compound No. | Q | $R^1$ | $R^2$ | T | U | 4,5-isomerism | Salt | melting point in °C. |
|---|---|---|---|---|---|---|---|---|
| 1.1 | N | Cl | Cl | $CH_3$ | $C_2H_5$ | cis | — | 81.1 |
| 1.2 | N | Cl | Cl | $CH_3$ | $C_2H_5$ | cis/trans | — | 109–113 |
| 1.3 | N | H | Cl | $CH_3$ | $C_2H_5$ | cis/trans | $HNO_3$ | — |
| 1.4 | N | Cl | Cl | $CH_3$ | $nC_3H_7$ | cis/trans | $HNO_3$ | 146.6 |
| 1.5 | N | H | Cl | $CH_3$ | $nC_3H_7$ | cis/trans | — | — |
| 1.6 | N | Cl | Cl | $C_2H_5$ | $C_2H_5$ | cis | $HNO_3$ | 160.9 |
| 1.7 | N | H | Cl | $C_2H_5$ | $C_2H_5$ | cis | — | — |
| 1.8 | N | Cl | Cl | $C_2H_5$ | $nC_3H_7$ | cis | HCl | — |
| 1.9 | N | H | Cl | $C_2H_5$ | $nC_3H_7$ | cis | — | — |
| 1.10 | N | Cl | Cl | $CH_3$ | $C_2H_5$ | cis | $CuCl_2$ | — |
| 1.11 | N | Cl | Cl | $C_2H_5$ | $C_2H_5$ | cis | $Mn(NO_3)_2$ | — |
| 1.12 | N | Cl | Cl | $CH_3$ | $nC_3H_7$ | cis | $ZnCl_2$ | — |
| 1.13 | N | Cl | Cl | $CH_3$ | $C_2H_5$ | cis | $ZnCl_2$ | — |
| 1.14 | N | Cl | Cl | $CH_3$ | $C_2H_5$ | cis | $Mn(NO_3)_2$ | — |
| 1.15 | N | Cl | Cl | $CH_3$ | $C_2H_5$ | cis/trans | $FeCl_3$ | — |
| 1.16 | N | Cl | Cl | $C_2H_5$ | $C_2H_5$ | cis | $CuCl_2$ | — |
| 1.17 | N | Cl | Cl | $C_2H_5$ | $C_2H_5$ | cis | $ZnCl_2$ | — |
| 1.18 | N | Cl | Cl | $C_2H_5$ | $C_2H_5$ | cis | $FeCl_3$ | — |
| 1.19 | N | Cl | Cl | $C_2H_5$ | $C_2H_5$ | cis/trans | $CuCl_2$ | — |
| 1.20 | CH | Cl | Cl | $CH_3$ | $C_2H_5$ | cis | — | oil |
| 1.21 | CH | H | Cl | $CH_3$ | $C_2H_5$ | cis/trans | — | viscous |
| 1.22 | CH | Cl | Cl | $CH_3$ | $nC_3H_7$ | cis | $HNO_3$ | — |
| 1.23 | CH | H | Cl | $C_2H_5$ | $C_2H_5$ | cis | — | — |
| 1.24 | CH | Cl | Cl | $C_2H_5$ | $C_2H_5$ | cis | $H_2SO_4$ | — |
| 1.25 | CH | Cl | Cl | $C_2H_5$ | $nC_3H_7$ | cis/trans | — | viscous |
| 1.26 | CH | Cl | Cl | $CH_3$ | $C_2H_5$ | cis | $(COOH)_2$ | — |
| 1.27 | CH | Cl | Cl | $CH_3$ | $C_2H_5$ | cis | $FeCl_3$ | — |
| 1.28 | CH | Cl | Cl | $CH_3$ | $C_2H_5$ | cis | $CuCl_2$ | — |
| 1.29 | CH | Cl | Cl | $C_2H_5$ | $C_2H_5$ | cis | $CuCl_2$ | — |
| 1.30 | CH | Cl | Cl | $CH_3$ | $nC_3H_7$ | cis | $CuCl_2$ | — |
| 1.31 | CH | Cl | Cl | $CH_3$ | $C_2H_5$ | cis | $Mn(NO_3)_2$ | — |
| 1.32 | CH | Cl | Cl | $CH_3$ | $C_2H_5$ | cis/trans | $CuCl_2$ | — |
| 1.33 | CH | Cl | Cl | $C_2H_5$ | $C_2H_5$ | cis | $Mn(NO_3)_2$ | — |
| 1.34 | CH | Cl | Cl | $C_2H_5$ | $C_2H_5$ | cis | $ZnCl_2$ | — |

-continued

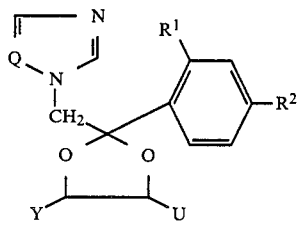

| Compound No. | Q | R¹ | R² | T | U | 4,5-isomerism | Salt | melting point in °C. |
|---|---|---|---|---|---|---|---|---|
| 1.35 | CH | Cl | Cl | C₂H₅ | C₂H₅ | cis/trans | CuCl₂ | — |
| 1.36 | CH | Cl | Cl | C₂H₅ | C₂H₅ | cis/trans | — | oil |

EXAMPLE II

A solution of 27 g (0.1 mole) of 2,4-dichlorophenacylbromide, 17.5 g (0.15 mole) of technical 1,2-cyclohexanediol (cis+trans isomer) and 0.5 g of 4-methylbenzenesulfonic acid in 200 ml of methylbenzene is refluxed during 8 hours using a water-separator. After cooling, the solution is washed with an aqueous sodium hydrogen carbonate solution and evaporated. The excess of 2,4-dichlorophenacylbromide is removed under reduced pressure (0.01 Torr) in an oil bath at 150°, yielding 30 g of 2-(bromomethyl)-2-(2,4-dichlorophenyl)hexahydrobenzodioxole as a viscous oil, containing mainly the cis-isomer.

30 g (0.082 mole) of 2-(bromomethyl)-2-(2,4-dichlorophenyl)hexahydrobenzodioxole are added to a stirred and heated (130°) mixture of 11 g (0.1 mole) of potassium tert. butoxide and 7 g (0.1 mole) of 1,2,4-triazole in dimethylformamide. After completion the reaction mixture is stirred for another 20 hours at 130°-140°. The dimethylformamide is evaporated under reduced pressure. The residue is taken up in water and extracted with a mixture of 1,1'-oxybisethane and ethyl acetate. The organic layer is separated, dried and evaporated yielding 25 g of a viscous resin, which is purified by columnchromatography over silica gel using dichloromethane as eluent. The pure fractions are collected and the eluent is evaporated, yielding 12 g of yellow resin, which corresponds with [2-(2,4-dichlorophenyl)-hexahydrobenzodioxol-2-ylmethyl]-1H-1,2,4-triazole according to the analytical and spectroscopical data.

EXAMPLE III

A. Following the same procedure as described in Example II part I and replacing the technical 1,2-cyclohexanediol (cis+trans isomers) by trans 1,2-cyclohexanediol there is also prepared: trans-[2-(2,4-dichlorophenyl)hexahydrobenzodioxol-2-ylmethyl]-1H-1,2,4-triazole as a viscous oil.

B. 5 g of 1,2,4-triazole (0.072 mole) and 4 g of pure potassium hydroxide is refluxed in absolute ethanol during 1 hour. The ethanol is evaporated under reduced pressure and the thus formed 1,2,4-triazole potassium salt is taken up in 200 ml of dimethylsulfoxide. 18.5 g (0.05 mole) of trans-[2-(2,4-dichlorophenyl)hexahydrobenzodioxol-2-ylmethyl]-1H-1,2,4-triazole is added and the whole is stirred during 8 hours at 140°. The reaction mixture is cooled and diluted with 1 l of water. The aqueous solution is extracted several times with 1,1'-oxybisethane, the organic layers are separated and the combined extracts are dried. While stirring, 4 ml of nitric acid (65%) are added, yielding white crystals.

The crystals are filtered off yielding 15 g of trans-[2-(2,4-dichlorophenyl)hexahydrobenzodioxol-2-ylmethyl]-1H-1,2,4-triazole nitrate; mp. 153°-155° C.

In a similar manner the following cis-ketals are prepared:

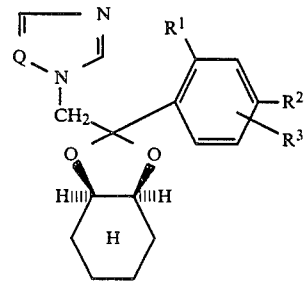

| Compound No. | R¹ | R² | R³ | Q | Salt/base | Melting point in °C. |
|---|---|---|---|---|---|---|
| 2.1 | Cl | Cl | H | CH | — | viscous |
| 2.2 | H | Cl | H | CH | — | — |
| 2.3 | H | Br | H | CH | — | — |
| 2.4 | Cl | H | Cl | CH | — | — |
| 2.5 | Cl | Cl | H | N | — | viscous |
| 2.6 | H | Cl | H | N | — | — |
| 2.7 | Br | Br | H | N | — | — |
| 2.8 | Cl | Cl | 5-Cl | N | — | — |
| 2.9 | Cl | Cl | H | CH | CuCl₂ | — |
| 2.10 | Cl | Cl | H | N | CuCl₂ | — |
| 2.11 | Cl | Cl | H | CH | Mn(NO₃)₂ | — |
| 2.12 | Cl | Cl | H | N | Mn(NO₃)₂ | — |

In a similar manner the following trans-ketals are prepared:

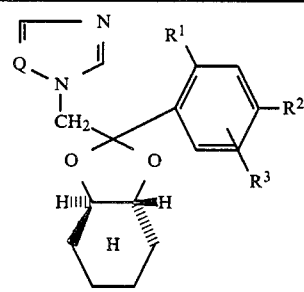

| Compound No | R¹ | R² | R³ | Q | Salt | Melting Point in °C. |
|---|---|---|---|---|---|---|
| 2.13 | Cl | Cl | H | CH | HNO₃ | 185-190(Z) |
| 2.14 | H | Cl | H | CH | — | — |
| 2.15 | Cl | Cl | H | N | HNO₃ | 153-155(Z) |

-continued

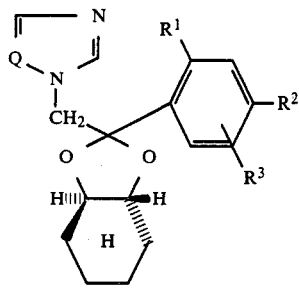

| Compound No. | R¹ | R² | R³ | Q | Salt | Melting Point in °C. |
|---|---|---|---|---|---|---|
| 2.16 | H | Cl | H | N | — | |
| 2.17 | Cl | Cl | 5-Cl | N | — | |
| 2.18 | Cl | Cl | H | CH | CuCl₂ | |
| 2.19 | Cl | Cl | H | CH | Mn(NO₃)₂ | |
| 2.20 | Cl | Cl | H | N | CuCl₂ | |
| 2.21 | Cl | Cl | H | N | Mn(NO₃)₂ | |

In a similar manner the following mixture of cis and trans ketal is prepared:

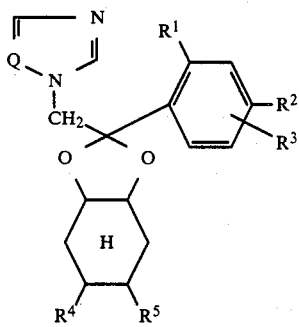

| Compound No. | R¹ | R² | R³ | Q | R⁴ | R⁵ | Salt/base | Melting point in °C. |
|---|---|---|---|---|---|---|---|---|
| 2.22 | Cl | Cl | H | N | CH₃ | H | — | viscous oil |

B. FORMULATION EXAMPLES

Example IV

Dusts: The following substances are used to prepare (a) 5% and (b) a 2% dust:

(a)
  5 parts of active substance
  95 parts of talc;

(b)
  2 parts of active substance
  1 part of highly dispersed silicic acid
  97 parts of talc.

The active substances are mixed with the carriers and ground and in this form can be processed to dusts for application.

Example V

Granulate: The following substances are used to prepare a 5% granulate:
  5 parts of active substance
  0.25 part of epichlorohydrin
  0.25 part of cetyl polyglycol ether
  3.25 parts of polyethylene glycol
  91 parts of kaolin (particle size 0.3–0.8 mm.).

The active substance is mixed with epichlorohydrin and the mixture is dissolved in 6 parts of 2-propanone. Then polyethylene glycol and cetyl polyglycol ether are added. The resultant solution is sprayed on kaolin and the 2-propanone is evaporated in vacuo. Such a microgranulate is advantageously used for combating soil fungi.

Example VI

Wettable powders: The following constituents are used to prepare (a) a 70%, (b) a 40%, (c) and (d) a 25% and (e) a 10% wettable powder:

(a)
  70 parts of active substance
  5 parts of sodium dibutylnaphthylsulfonate
  3 parts of naphthalenesulfonic acid/phenolsulfonic acid/formaldehyde condensate (3:2:1).
  10 parts of kaolin
  12 parts of Champagne chalk.

(b)
  40 parts of active substance
  5 parts of sodium ligninsulfonate
  1 part of sodium dibutylnaphthalenesulfonic acid
  54 parts of silicic acid.

(c)
  25 parts of active substance
  4.5 parts of calcium ligninsulfonate
  1.9 parts of Champagne chalk/hydroxyethyl cellulose mixture (1:1)
  1.5 parts of sodium dibutylnaphthalenesulfonate
  19.5 parts of silicic acid
  19.5 parts of Champagne chalk
  28.1 parts of kaolin (d)
  25 parts of active substance
  2.5 parts of isooctylphenoxy-polyethylene-ethanol
  1.7 parts of a Champagne chalk/hydroxyethyl cellulose mixture (1:1)
  8.3 parts of sodium aluminium silicate
  16.5 parts of kieselguhr
  46 parts of kaolin (e)
  10 parts of active substance
  3 parts of a mixture of the sodium salts of saturated fatty alcohol sulfates
  5 parts of naphthalenesulfonic acid/formaldehyde condensate
  82 parts of kaolin.

The active substances are intimately mixed in suitable mixers with the additives and ground in appropriate mills and rollers. Wettable powders of excellent wettability and suspension powder are obtained. These wettable powders can be diluted with water to give suspensions of the desired concentration and can be used in particular for leaf application

Example VII

Emulsifiable concentrates: the following substances are used to prepare a 25% emulsifiable concentrate:
  25 parts of active substance
  2.5 parts of epoxidized vegetable oil
  10 parts of an alkylarylsulfonate/fatty alcohol polyglycol ether mixture
  5 parts of dimethyl formamide
  57.5 parts of dimethylbenzene.

By diluting such a concentrate with water it is possible to prepare emulsions of the desired concentration, which are especially suitable for leaf application.

C. BIOLOGICAL EXAMPLES

Example VIII

Activity against *Cercospora personata* (= *Cercospora arachidicola*) on ground-nut plants Ground-nut plants, 3 weeks old, are sprayed with a spray broth (containing 0.02% of active substance), prepared from a wettable powder of the active substance. After about 12 hours the treated plants are infected by dusting them with a suspension of conidia of the fungus. The infected plants are then incubated for about 24 hours at 22° C. at a high relative humidity (>90%) and then stood in the glass-house. Fungal infection is evaluated 12 days after the day of infection on basis of the number and the extend of the appearing spots. In comparison with untreated plants those, treated with a compound of formula (I), display only limited growth of the fungus or no growth at all. The compounds nos. 1.1, 1.2, 1.6, 1.10, 1.11, 1.13 to 1.19 and 2.5 inhibit the growth of the fungus at a concentration of 0.002%.

Example IX

Activity against *Puccinia graminis* on wheat (a) Residual-protective action

Wheat plants were sprayed 6 days after sowing with a spray broth (0.06% of active substance) prepared from a wettable powder of the active substance. After 24 hours the treated plants were infected with a suspension of Uredospores of the fungus. After an incubation period of 48 hours at 95–100% relative humidity and at about 20° C. the plants were stood in a greenhouse at approx. 22° C. The development of rust-pustules was evaluated 12 days after the infection. The compounds of formula (I) display a strong fungicidal activity. The compounds nos. 2.5 and 2.15 inhibit the growth of the fungus even at a concentration of 0.006%.

(b) Systemic action

5 Days after sowing wheat plants are sprayed with a spray broth (containing 0.006% of active substance; the amount of the spray being proportional with the soil-volume) prepared from a wettable powder of the active substance. After 3 days the treated plants are infected with a suspension of Uredospores of the fungus. After an incubation period of 48 hours at 95–100% relative humidity and at 20° C. the treated plants are stood in a glass-house at about 22° C. The rust-pustules are evaluated 12 days after the day of infection. The compounds of formula (I) display strong fungicidal activity The compound nos. 1.1, 1.2, 1.6, 1.10, 1.11, 2.5, 2.15 and 2.22 inhibit the growth of the fungus completely, the compounds nos. 2.5 and 2.15 inhibit the growth of the fungus at a concentration of 0.0006% (relative to the soil volume).

Example X

Residual-protective action against *Venturia inaequalis* on apple seedlings

Apple seedlings, being 10–20 cm in height, are sprayed with a spray broth (containing 0.06% of active substance), prepared from a wettable powder of the active substance. After 21 hours the treated plants are infected with a suspension of conidia of the fungus. The plants are then incubated at 90–100% relative humidity and subsequently during 10 days in a greenhouse at 20°–24° C. The fungal infection is evaluated 15 days after the day of infection. The compounds of formula (I) display strong fungicidal activity. The compounds nos. 1.1, 1.2, 1.6, 1.10, 1.11, 2.22 and others inhibit the growth of the fungus at a concentration of 0.006%, the compounds nos. 2.5 and 2.15 even at a concentration of 0.0006%.

Example XI

Residual protective action against *Podosphaera leucotricha* on apple seedlings

Apple seedlings, being 15 cm in height, are sprayed with a spray broth (containing 0.06% active substance) prepared from a wettable powder of the active substance. After 24 hours the treated plants are infected with a suspension of conidia of the fungus and the infected plants are stood in a growth-chamber at 70% relative humidity and at 20° C. The fungal infection is evaluated 12 days after the day of infection. The compounds of formula (I) display a strong fungicidal activity. The compounds nos. 1.1, 1.2, 1.6, 1.10, 1.11, 2.5, 2.15 and others inhibit the growth of the fungus at a concentration of 0.006%.

Example XII

Activity against *Erysiphe graminis* on barley (a) Residual-protective action

Barley plants, about 8 cm in height, are sprayed with a spray broth (containing 0.02% of active substance) prepared from a wettable powder of the active substance. After 3–4 hours the treated plants are dusted with conidia of the fungus. The infected barley plants are then placed in a glass-house at about 22° C. and fungal attack is evaluated 10 days after the day of infection.

(b) Systemic action

A spray broth (containing 0.006% of the active substance; the amount being proportional with the soil-volume), prepared from a wettable powder of the active substance is administered to barley plants, about 8 cm in height, while care is taken that the external parts of the plants do not enter into contact with the spray. After 48 hours the treated plants are dusted with conidia of the fungus. The infected barley plants are stood in a glass-house at 22° C. and the fungal infection is evaluated after 10 days. In experiments (a) and (b) the compounds of formula (I) inhibit the growth of the fungus completely. The compounds nos. 1.1 to 1.4, 1.6, 1.8, 1.10 to 1.19, 2.1, 2.2, 2.4, 2.5, 2.6, 2.9, 2.10, 2.13, 2.15, 2.18 and 2.22 inhibit the growth of the fungus in experiment (a) even at a concentration of 0.002%. The compounds nos. 1.1 and 1.2 inhibit the growth of the fungus in experiment (b) even at a concentration of 0.002%, the compounds nos. 2.5 and 2.15 even at a concentration of 0.0002%.

Example XIII

Activity against *Botrytis cinerea* on broad beans

Broad bean plants, about 10 cm in height, are sprayed with a spray broth (containing 0.02% of active substance) prepared from a wettable powder of the active substance. After 48 hours the treated plants are infected with a suspension of conidia of the fungus. After incubating the infected plants for 3 days at 95–100% relative humidity and at 21° C. the fungal infection is evaluated. The compounds of formula (I) inhibit the growth of the fungus completely. Even at a concentration of 0.006% the compounds nos. 1.1, 1.2, 1.4, 1.6, 2.1 and 2.13 display a complete activity.

What is claimed is:

1. A chemical compound selected from the group consisting of an azole derivative having the formula and the phytopharmaceutically acceptable acid addition salts, metal salt complexes and stereochemically isomeric forms thereof, wherein $R^1$, $R^2$ are both chloro and $R^3$ is hydrogen;
Q is N;
T is a member selected from the group consisting of methyl and ethyl;
U is a member selected from the group consisting of ethyl and propyl.

2. A chemical compound selected from the group consisting of [2-(2,4-dichlorophenyl)-4-ethyl-5-methyl-1,3-dioxolan-2-ylmethyl]-1H-1,2,4-triazole and the phytopharmaceutically acceptable acid addition salts, metal salt complexes and stereochemically isomeric forms thereof.

3. A composition for combating fungi comprising an inert carrier material and as an active ingredient an effective antifungal amount of a compound selected from the group consisting of an azole derivative having the formula and the phytopharmaceutically acceptable acid addition salts, metal salt complexes and stereochemically isomeric forms thereof, wherein $R^1$, $R^2$ are both chloro and $R^3$ is hydrogen;
Q is N;
T is a member selected from the group consisting of methyl and ethyl;
U is a member selected from the group consisting of ethyl and propyl.

4. A composition for combating fungi comprising an inert carrier material and as an active ingredient an effective antifungal amount of a compound selected from the group consisting of [2-(2,4-dichlorophenyl)-4-ethyl-5-methyl-1,3-dioxolan-2-ylmethyl]-1H-1,2,4-triazole and the phytopharmaceutically acceptable acid addition salts, metal salt complexes and stereochemically isomeric forms thereof.

5. A method of combating fungi which comprises contacting said fungi with an effective antifungal amount of a compound selected from the group consisting of an azole derivative having the formula and the phytopharmaceutically acceptable acid addition salts, metal salt complexes and stereochemically isomeric forms thereof, wherein $R^1$, $R^2$ are both chloro and $R^3$ is hydrogen;
Q is N;
T is a member selected from the group consisting of methyl and ethyl;
U is a member selected from the group consisting of ethyl and propyl.

6. A method of combating fungi which comprises contacting said fungi with an effective antifungal amount of a compound selected from the group consisting of [2-(2,4-dichlorophenyl)-4-ethyl-5-methyl-1,3-dioxolan-2-ylmethyl]-1H-1,2,4-triazole and the phytopharmaceutically acceptable acid addition salts, metal salt complexes and stereochemically isomeric forms thereof.

* * * * *